United States Patent [19]

Jessel, Jr. et al.

[11] Plant 4,555

[45] Jun. 24, 1980

[54] CHRYSANTHEMUM PLANT CULTIVAR NAME: VANGUARD

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 10,857

[22] Filed: Feb. 9, 1979

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Donald D. Jeffery

[57] ABSTRACT

A chrysanthemum plant known by the cultivar name Vanguard and particularly characterized as to uniqueness by the combined characteristics of flat capitulum form twisting with age; decorative capitulum type; dark yellow ray floret color; diameter across face of capitulum ranging from 70 to 90 mm. at maturity; uniform nine week photoperiodic flowering response to short days; short plant height when grown as a pinched spray pot, and spreading branching pattern.

7 Drawing Figures

The present invention comprises a new and distinct cultivar of *Chrysanthemum morifolium*, Ramat., hereinafter referred to by the cultivar name Vanguard.

Vanguard is a product of a planned breeding program which had the objective of creating new chrysanthemum cultivars with decorative capitulum type, with yellow floret color, with eight or nine week flowering response, with short plant height, and with the ability to produce commercially acceptable quality in year round pot mum programs. Such traits in combination were not present in previously available commercial cultivars.

Vanguard was originated from a cross made in a controlled breeding program in Barberton, Ohio in 1973. The female parent was #70350001 (unnamed seedling), a yellow decorative originated by the present inventors from a cross between #67491010 (unnamed seedling) and Sunstar (unpatented; commercially available). The male parent of Vanguard was Resplendent (unpatented; commercially available), a lavender decorative originated by the present inventors from a cross between Mandalay (unpatented; commercially available) and #22005E04 (unnamed seedling). #67491010, Sunstar, Mandalay, and #22005E04 are products of the breeding program of the present inventors.

Vanguard was discovered and selected as one flowering plant within the progeny of the stated cross by Walter H. Jessel, Jr. and William E. Duffett on Jan. 31, 1975 in a controlled environment in Barberton, Ohio.

The first act of asexual reproduction of Vanguard was accomplished when vegetative cuttings were taken from the initial selection in July, 1975 in a controlled environment in Barberton, Ohio, by a technician working under formulations established and supervised by Walter H. Jessel, Jr. and William E. Duffett. Horticultural examination of selected units initiated Sept. 25, 1975 has demonstrated that the combination of characteristics as herein disclosed for Vanguard are firmly fixed and are retained through successive generations of asexual reproduction.

Vanguard has not been observed under all possible environmental conditions. The phenotype may vary significantly with variations in environment such as temperature, light intensity, and daylength. The following observations, measurements, and comparisons describe plants grown in Barberton, Ohio and in Salinas, Calif. under greenhouse conditions which approximate those generally used in commercial practice.

The following traits have been repeatedly observed and are determined to be basic characteristics of Vanguard which in combination distinguish this chrysanthemum as a new and distinct cultivar:

(1) Flat capitulum form, with the ray florets twisting longitudinally with maturity.

(2) Decorative capitulum type.

(3) Dark yellow ray floret color, devoid of bronze overtones.

(4) Diameter across face of capitulum ranging from 70 to 90 mm. at maturity.

(5) Uniform nine week photoperiodic flowering response to short days.

(6) Short plant height (requiring 2–3 long day weeks prior to pinch and short days, and 1 application 2500 ppm B-9 SP 21 days after the beginning of short days to attain a flowered plant height of 30 to 45 cm).

(7) Spreading branching pattern.

The accompanying photographic drawings show typical inflorescence and foliage characteristics of Vanguard. Sheet 1 is a color photograph of a specimen pot of Vanguard. Some difficulty was encountered in obtaining accurate color depiction of ray floret color, with the photograph being less yellow and more red than the actual ray floret color. The color readings specified within the following text are, however, accurate. Sheet 2 is a black and white photograph showing three views of the capitulum of Vanguard. Sheet 3 is a black and white photograph showing the foliage of Vanguard at three stages of growth.

Of the many commercial cultivars known to the present inventors, the most similar in comparison to Vanguard are Sunny Mandalay, disclosed in U.S. Plant Pat. No. 3,231, and Yellow Torch, disclosed in U.S. Plant Pat. No. 3,421. Reference is made to attached Chart A which compares certain characteristics of Vanguard to those same characteristics of Sunny Mandalay and Yellow Torch. General comparisons are as follows:

(1) In comparison to Sunny Mandalay, Vanguard has less incurved capitulum form, more spreading branching pattern, smaller diameter across face of capitulum, shorter plant height, and earlier flowering response period. The ray floret color, and capitulum type of Vanguard are similar to those same characteristics of Sunny Mandalay.

(2) In comparison to Yellow Torch, Vanguard has less bronze overtones to ray floret color, and more spreading branching pattern. The capitulum form, capitulum type, diameter across face of capitulum, plant height, and flowering response period of Vanguard are similar to those same characteristics of Yellow Torch.

In the following description, color references are made to A Limit Color Cascade, by the Munsell Company, 1972 edition. The color values were determined between 10:00 and 10:30 A.M. on Nov. 2, 1978 under 100 foot-candle light intensity at Salinas, Calif.

Botanical classification: *Chrysanthemum morifolium,* Ramat., cv Vanguard

INFLORESCENCE

A. Capitulum:
- *Form.*—Flat, with ray florets twisting longitudinally with maturity.
- *Type.*—Decorative.
- *Diameter across face.*—70 to 90 mm.

B. Corolla of ray florets:
- *Color (general tonality).*—Dark yellow, 26-6.
- *Color (abaxial).*—25-6 to 25-4.
- *Color (adaxial).*—25-4 to 25-3.
- *Persistence.*—Resists shatter.

C. Reproductive organs:
- *Androecium.*—Present disc florets only; scant to few; scant pollen.
- *Gynoecium.*—Present both ray and disc florets.

PLANT

A. General appearance: Spreading branching pattern; short height.

B. Foliage:
- *Color (abaxial).*—Approximately 20-14.

- *Color (adaxial).*—Approximately 21-13 overlaid with white.

CHART A

COMPARISON OF VANGUARD, SUNNY MANDALAY AND YELLOW TORCH

| CULTIVAR | RAY FLORET COLOR | CAPITULUM FORM AND TYPE | BRANCHING PATTERN |
|---|---|---|---|
| Vanguard | Dark Yellow | Flat Decorative | Spreading |
| Sunny Mandalay | Dark Yellow | Semi-incurved Decorative | Semi-spreading |
| Yellow Torch | Dark Yellow with bronzy overtones | Flat Decorative | Semi-upright |

| CULTIVAR | DIAMETER ACROSS FACE OF CAPITULUM | PLANT HEIGHT | FLOWERING RESPONSE PERIOD |
|---|---|---|---|
| Vanguard | 70 to 90 mm. | Short | 9 week |
| Sunny Mandalay | 85 to 100 mm. | Medium | 10 week |
| Yellow Torch | 75 to 90 mm. | Short | 9 week |

COMPARISONS MADE OF PLANTS GROWN AS PINCHED SPRAY POTS IN BARBERTON, OHIO AND IN SALINAS, CALIFORNIA.

We claim:

1. A new and distinct cultivar of *Chrysanthemum morifolium,* Ramat., plant as shown and described, known by the cultivar name Vanguard and particularly characterized as to uniqueness by the combined characteristics of flat capitulum form, twisting at maturity; decorative capitulum type; dark yellow ray floret color, devoid of bronze overtones; diameter across face of capitulum ranging from 70 to 90 mm. at maturity; uniform nine week flowering response; tall plant height; and spreading branching pattern.

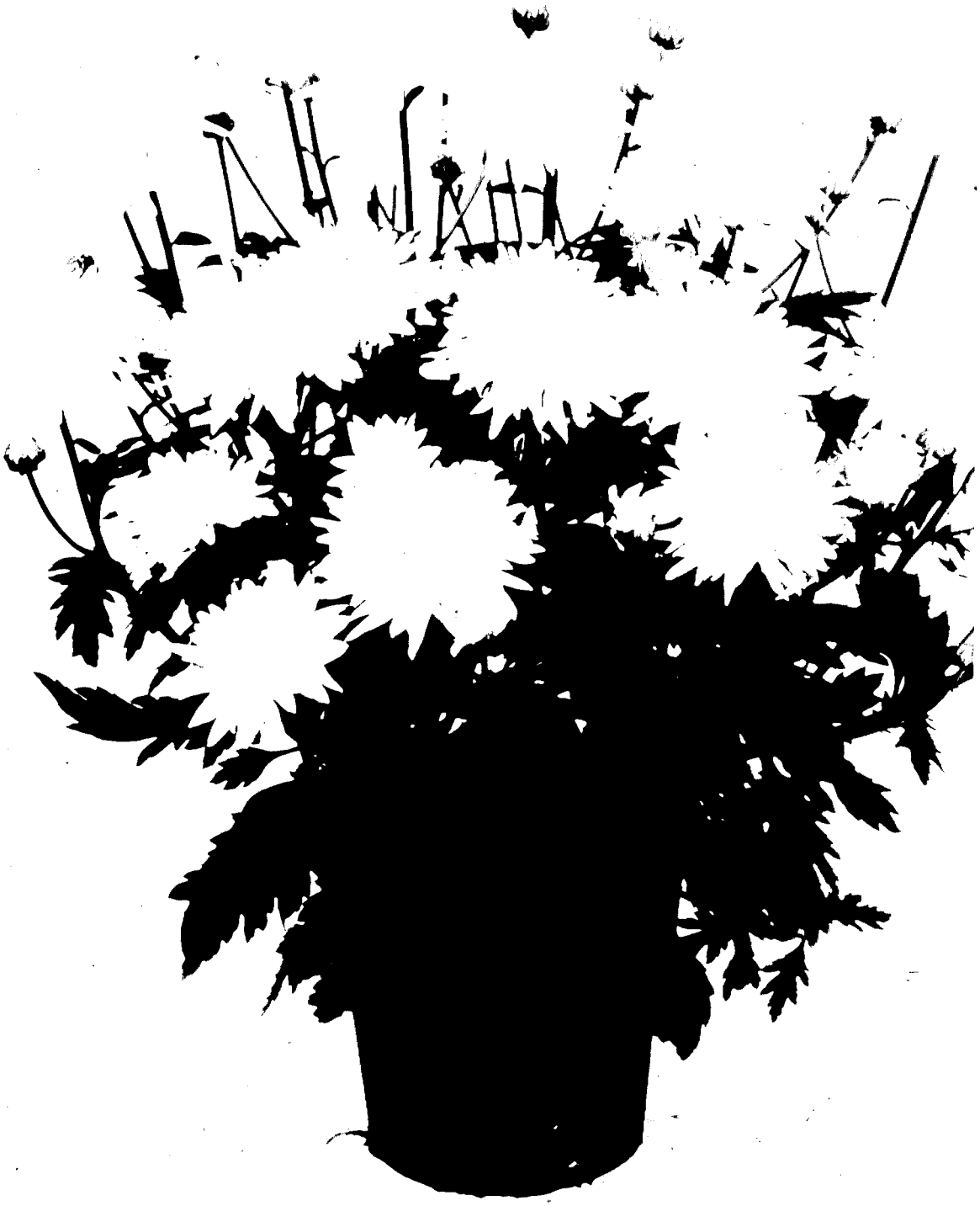

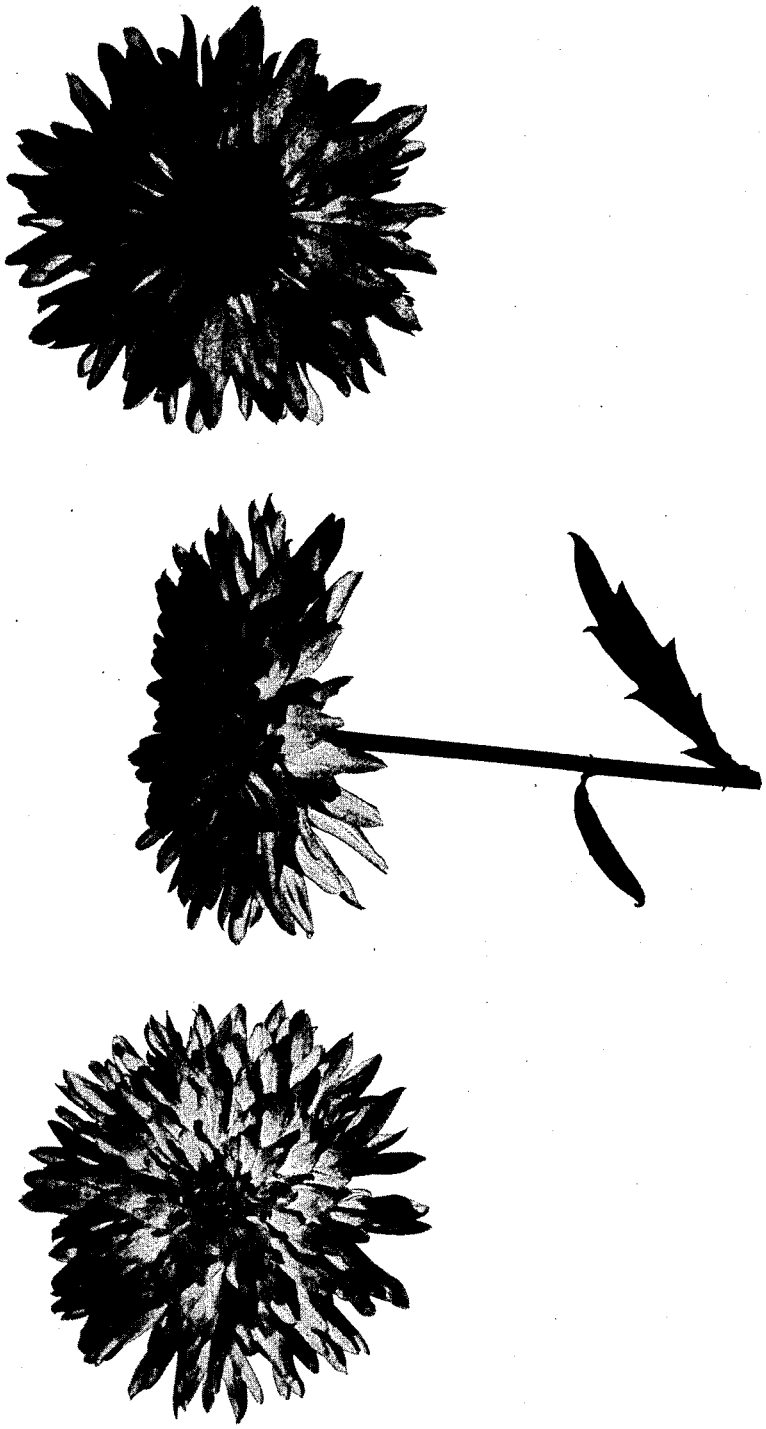

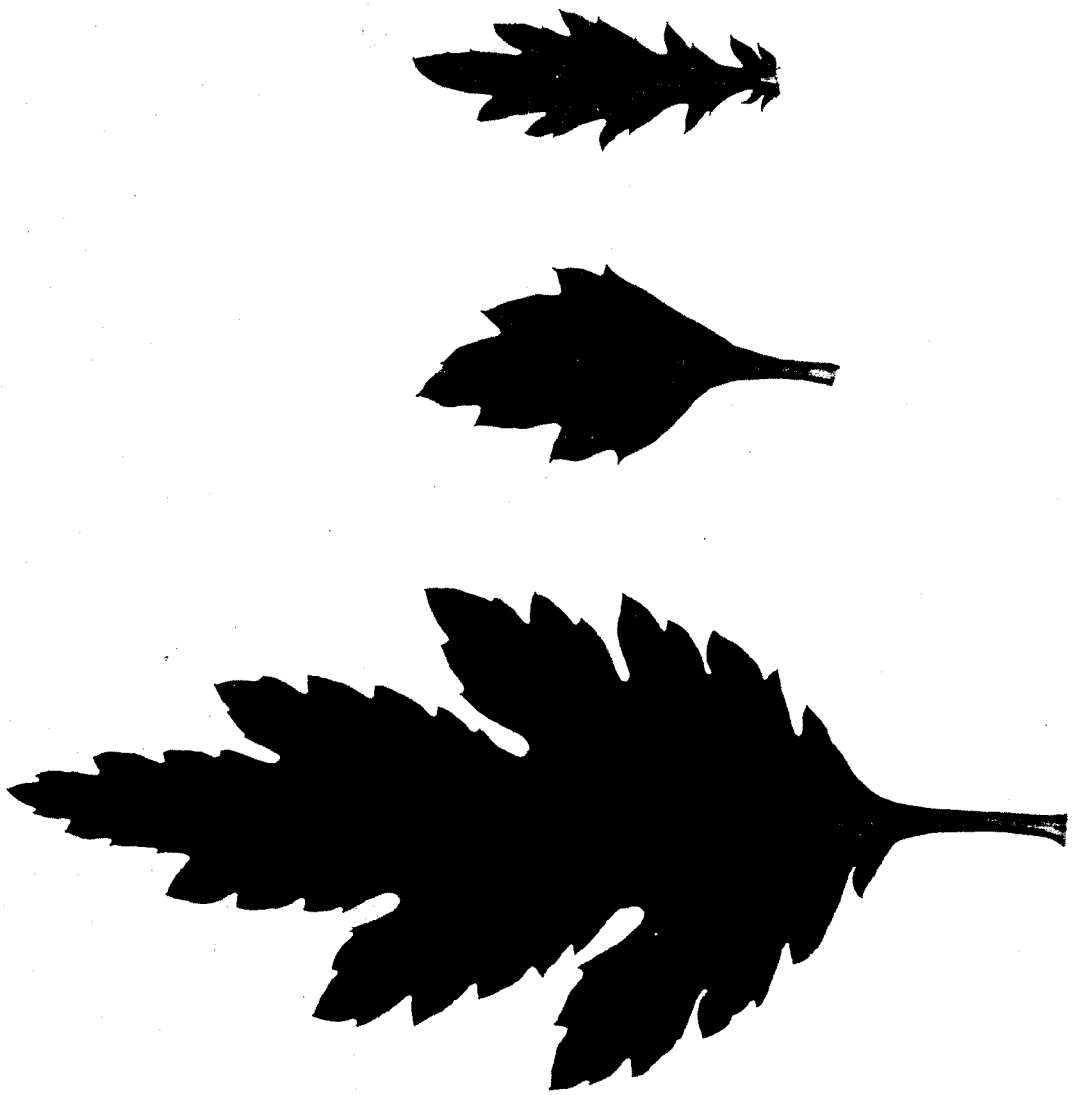

* * * * *